US012565623B2

(12) United States Patent
Nedwed et al.

(10) Patent No.: US 12,565,623 B2
(45) Date of Patent: Mar. 3, 2026

(54) METHODS FOR BIOTECHNOLOGICAL CONVERSION OF NATURAL GAS INTO ANIMAL FEED AS A SUBSTITUTE FOR FLARING AND RELATED SYSTEMS

(71) Applicant: ExxonMobil Technology and Engineering Company, Spring, TX (US)

(72) Inventors: Timothy J. Nedwed, Houston, TX (US); Lin Zhao, Spring, TX (US); Sam Aminfard, Houston, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 793 days.

(21) Appl. No.: 18/051,676

(22) Filed: Nov. 1, 2022

(65) Prior Publication Data

US 2023/0151289 A1 May 18, 2023

Related U.S. Application Data

(60) Provisional application No. 63/264,112, filed on Nov. 16, 2021.

(51) Int. Cl.
*C10L 3/10* (2006.01)
*C12M 1/107* (2006.01)

(52) U.S. Cl.
CPC ............... *C10L 3/10* (2013.01); *C12M 21/04* (2013.01)

(58) Field of Classification Search
None
See application file for complete search history.

(56) References Cited

FOREIGN PATENT DOCUMENTS

WO WO-2022025820 A1 * 2/2022 ............. F24D 18/00

* cited by examiner

*Primary Examiner* — Daniel Berns
(74) *Attorney, Agent, or Firm* — Troutman Pepper Locke LLP

(57) ABSTRACT

Methods include providing a natural gas stream; directing a first fraction of the natural gas stream to a bioreactor including a propagating culture of hydrocarbon degrading microbes; directing a second fraction of the gas stream to a local power generator and converting the natural gas stream to electricity and heat; using a dynamic control system to balance of the gas stream to the first fraction and the second fraction based on one or more of the availability of electricity from an electricity grid and the price of electricity from the electricity grid; powering, at least in part, the bioreactor with the electricity generated by the local power generator; and harvesting the hydrocarbon degrading microbes from the bioreactor as a biomass. Related systems are also provided.

18 Claims, 3 Drawing Sheets

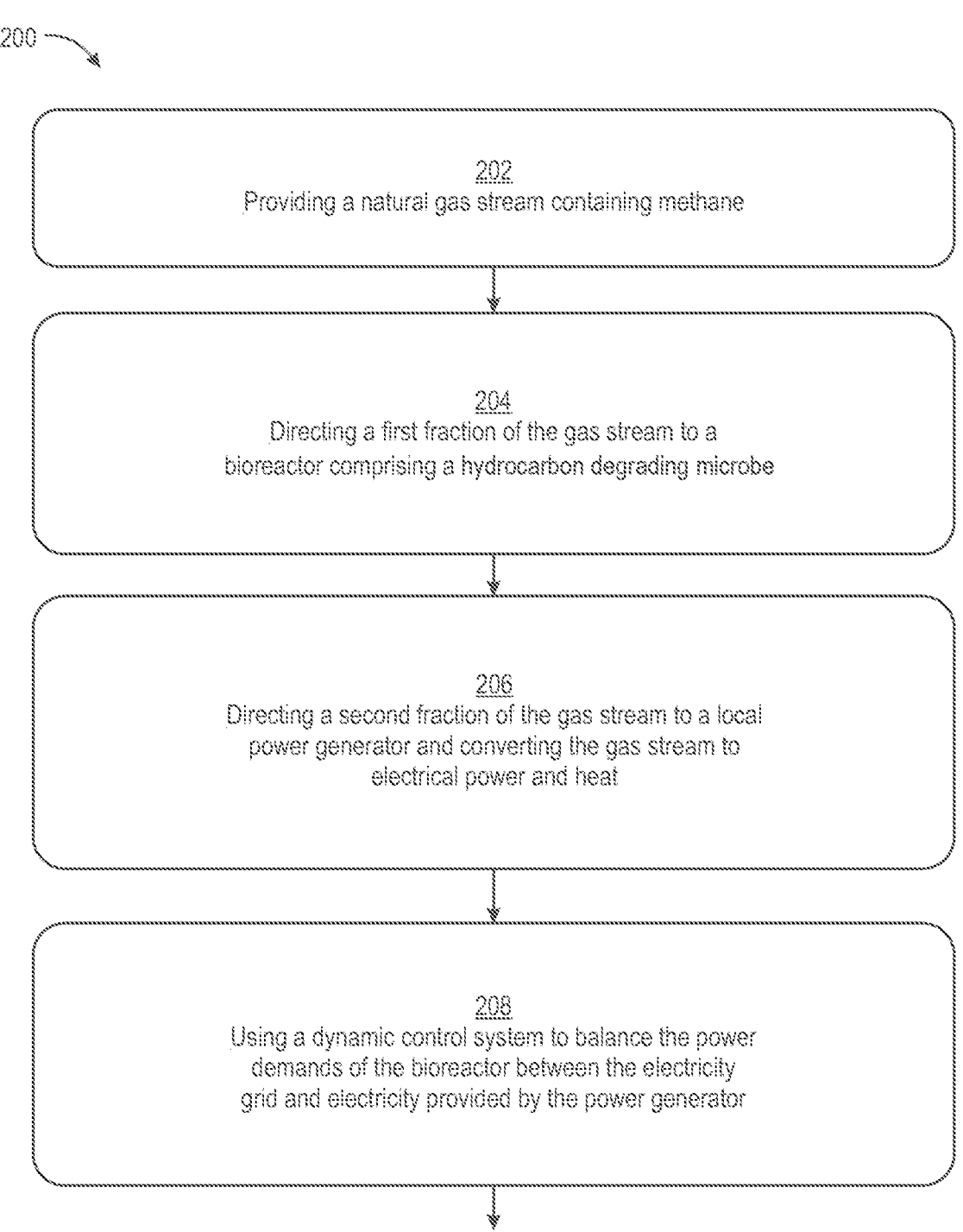

200

202
Providing a natural gas stream containing methane

204
Directing a first fraction of the gas stream to a
bioreactor comprising a hydrocarbon degrading microbe 206
Directing a second fraction of the gas stream to a local
power generator and converting the gas stream to
electrical power and heat 208
Using a dynamic control system to balance the power
demands of the bioreactor between the electricity
grid and electricity provided by the power generator

FIG. 2A

From 208

210
Powering the bioreactor, at least in part, with the
electricity generated by the local power generator 212
Harvesting a biomass from the bioreactor

METHODS FOR BIOTECHNOLOGICAL CONVERSION OF NATURAL GAS INTO ANIMAL FEED AS A SUBSTITUTE FOR FLARING AND RELATED SYSTEMS

CROSS-REFERENCE TO RELATED APPLICATION

This application claims the benefit of U.S. Provisional Application Ser. No. 63/264,112, entitled "Methods for Biotechnological Conversion of Natural Gas Into Animal Feed as a Substitute for Flaring and Related Systems", filed Nov. 16, 2021, the disclosure of which is hereby incorporated by reference in its entirety.

FIELD OF THE INVENTION

The presently disclosed subject matter relates to systems and methods for converting natural gas produced during hydrocarbon production into biomass as an alternative to flaring or disposal.

BACKGROUND OF THE INVENTION

Natural gas is often produced along with oil during hydrocarbon production. Typically, the oil has the higher market value and is far easier to transport by tankers. Accordingly, at hydrocarbon production sites, produced oil is separated from produced natural gas to maximize economic return for transport costs. The produced oil is then directed to a location, such as a refinery for further processing. When gas markets are accessible, the produced natural gas is often transported to these markets by tanker or pipeline.

However, if a gas market is not readily accessible, which is often the case for remote production sites far from population centers or efficient transport access, the gas product is considered "stranded." The inability to market the natural gas provides operators with limited options to avoid shutting down production as inventories accumulate. One option is to flare (or burn) the natural gas on-site. In some instances, a fraction of the natural gas may be consumed on site for electrical energy or injected back into the hydrocarbon formation for enhanced oil recovery (EOR) processes. While efficient use of the natural gas is preferred, economical and technical constraints often result in disposal by flaring, which produces carbon dioxide and contributes to greenhouse gas emissions.

Alternative productive uses of natural gas that can be economically implemented at hydrocarbon production sites and that reduce carbon dioxide emissions would be of value to the industry.

SUMMARY OF THE INVENTION

Methods disclosed herein include systems and methods for converting natural gas produced during hydrocarbon production into biomass as an alternative to flaring or other disposition methods.

In one aspect, methods include providing a natural gas stream; directing a first fraction of the natural gas stream to a bioreactor comprising hydrocarbon degrading microbes; directing a second fraction of the stream to a local power generator and converting the natural gas stream to electricity and heat; powering, at least in part, the bioreactor with the electricity generated by the local power generator; and harvesting the hydrocarbon degrading microbes from the bioreactor as a biomass.

In another aspect, methods include providing a natural gas stream; directing a first fraction of the natural gas stream to a bioreactor comprising a propagating culture of hydrocarbon degrading microbes; directing a second fraction of the gas stream to a local power generator and converting the natural gas stream to electricity and heat; using a dynamic control system to balance of the gas stream to the first fraction and the second fraction based on one or more of the availability of electricity from an electricity grid and the price of electricity from the electricity grid; powering, at least in part, the bioreactor with the electricity generated by the local power generator; and harvesting the hydrocarbon degrading microbes from the bioreactor as a biomass.

In another aspect, systems include a natural gas stream; a bioreactor propagating hydrocarbon degrading microbes and receiving at least a portion of the natural gas stream; a local power generator receiving at least a portion of the natural gas stream, the power generator connected to the bioreactor and providing at least a portion of electrical power thereto; an electricity grid connected to the bioreactor and capable of providing at least a portion of electrical power thereto; and a dynamic control system connected to the bioreactor, the local power generator, and the electricity grid, the dynamic control system controlling amount of electrical power output from the power generator and the electricity grid to the bioreactor based on one or more user inputs.

BRIEF DESCRIPTION OF THE DRAWINGS

FIGS. 2A and 2B are flow diagrams depicting a method of conversion of natural gas to biomass in accordance with the present disclosure.

DETAILED DESCRIPTION OF THE INVENTION

The presently disclosed subject matter relates to systems and methods for converting natural gas produced during hydrocarbon production into biomass as an alternative to flaring or other disposition methods. Systems disclosed herein may include configurations for delivering natural gas to a parallel system of power generators and bioreactors containing a propagating microorganism to create biomass suitable for processing into a single cell protein feedstock. Methods disclosed herein may also include the use of dynamic control systems that balance the electricity requirements for bioreactor operation with local power generation to improve the economics of natural gas bioconversion and reducing greenhouse gas emissions.

As used herein, "natural gas" refers to naturally occurring gas mixtures that have formed in subterranean reservoirs and can be accessed by conventional processes (e.g., drilling). Natural gas may also be sourced from various laboratory and/or industrial processes (e.g., wastewater treatment, landfills). Natural gas may contain a primary component of methane, but may also may have one or more additional components of light alkane gases (e.g., ethane, propane, butane, pentane), carbon dioxide, nitrogen, hydrogen sulfide, or the like, or any combination thereof.

As used herein, a "single cell protein" (SCP) refers to a protein source derived from a microbial biomass for use in food products and/or animal feeds.

Systems and methods disclosed herein provide economically viable alternatives to the disposal of natural gas obtained during hydrocarbon production. Particularly, "stranded" natural gas produced in remote regions with minimal or negative market value after production and transport cost may be diverted to processes that convert light alkanes such as methane to SCP. In addition, methods may also include reducing the operating costs for SCP production by utilizing a portion of the natural gas for local power generation.

Figure 1:
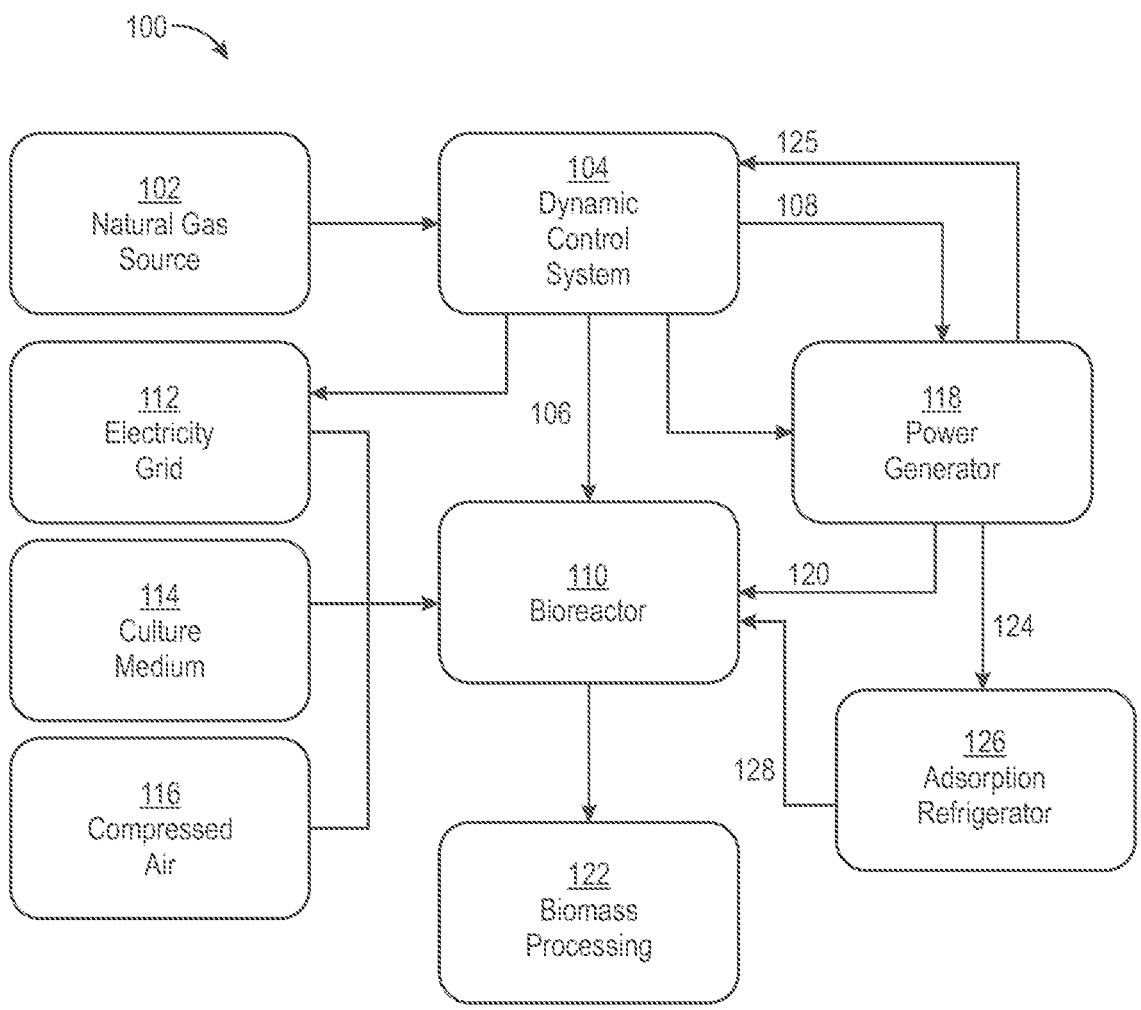
FIG. 1 is a schematic diagram showing a system for managing the conversion of natural gas to biomass in accordance with the present disclosure.

An overall schematic depicting an example system 100 that utilizes hydrocarbon degrading microbes to convert natural gas to SCP is shown in FIG. 1. A natural gas source 102 source may be routed through a dynamic control system 104 that partitions the incoming gas source 102 into Streams 106 and 108. Stream 106 is input to bioreactor 110 housing propagating hydrocarbon degrading microbes, which consume components of the natural gas stream, particularly methane, to produce cellular matter, carbon dioxide, and heat. In some embodiments, natural gas stream 106 may be cleaned to remove any contaminants if present, and compressed and delivered to the bioreactor 110. Other reagents and nutrients needed for growth of the hydrocarbon degrading microbes are also added, such as culture medium 114 and compressed air 116.

Bioreactor 110 may be a single unit or a zone containing multiple units. Suitable bioreactors 110 may include those that are known to those of ordinary skill in the art of large scale microbial culturing, such as stirred tank bioreactors; shake tank bioreactors; hollow fiber bioreactors; fluidized bed bioreactors; airlift reactors; biological scrubber columns; bubble columns; counter-current, upflow, and expanded-bed reactors; digesters; filters such as trickling filters, rotating biological contactor filters, rotating discs, soil filters; fluidized bed reactors; gas lift fermenters; immobilized cell reactors; loop reactors/U-loop reactors; membrane biofilm reactors; pachuca tanks; packed-bed reactors; plug-flow reactors; static mixers; trickle bed reactors; vertical shaft bioreactors; and the like; and combinations thereof. Bioreactors 110 disclosed herein may operate in a batch, fed batch, continuous, semi-continuous, or perfusion mode.

Suitable hydrocarbon degrading microbes include naturally occurring (wild type) and/or genetically modified microorganisms (GMO) capable of metabolizing various hydrocarbon found in natural gas, including methane, ethane, propane, and the like. In some embodiments, hydrocarbon degrading microbes may include bacteria, archaea, fungi, and combinations thereof. Hydrocarbon degrading microbes may consume one or more hydrocarbons of the natural gas and using one or more biological pathways. An example of a typical metabolic process for degrading methane is shown in Eq. 1.

$$CH_4 + 1.5O_2 + 0.1NH_3 \rightarrow 0.1C_5H_7O_2N + 0.5CO_2 + 1.8H_2O + 643 \text{ kJ} \qquad \text{(Eq. 1)}$$

In other examples, hydrocarbon degrading microbes may combine oxygen and methane to form formaldehyde, or oxidize methane anaerobically. In some embodiments, hydrocarbon degrading microbes may utilize a syntrophic partner that performs a portion of the reaction to convert hydrocarbons and other natural gas components. While hydrocarbon degrading microbes described herein may sometimes be referred to as "methanotrophic" in this paper and the field, such microbes may also be facultative to higher number hydrocarbons (e.g., ethane, propane, butane, and the like) and no limitation is implied that the microbes are limited to use with hydrocarbon streams containing only methane.

In certain embodiments, the present disclosure provides hydrocarbon degrading microbes from the genera including *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Gammaproteobacteri, Alphaproteobacteria, Methylacidiphilaceae, Methanosarcinales, Methanomicrobiales, Methanopyrales, Methanococcales,* and the like. Exemplary hydrocarbon degrading microbes may include bacteria such as *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11, 198), *Methylomonas methanica* (NRRL B-11,199), *Methylomonas albus* (NRRL B-11,200), *Methylobacter capsulatus* Y (NRRL B-11,201), *Methylococcus capsulatus* (NCIMB 11132), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petrolelphdum, Methylobacterium populi, Brevibacillus agri, Ralstonia* sp., *Aneurinibacillus* sp., methylotrophs such as *Methylobacterium extorquens, Methylobacterium radiotolerans, Methylobacterium populi, Methylobacterium chloromethanicum, Methylobacterium nodulans,* and the like, and combinations thereof. Hydrocarbon degrading microbes may also include eukaryotes such as yeasts from the genera *Candida, Yarrowia, Hansenula, Pichia, Torulopsis,* or *Rhodotorula.*

The metabolic activity of the hydrocarbon degrading microbes within bioreactor 110 generates considerable heat, which requires substantial amounts of electricity consumption to dissipate. Heat dissipation may be effected by any suitable method, such as refrigeration, heat exchange, and the like. Electrical consumption in bioreactor 110 is also attributed to a number of systems required for operation. Systems can vary depending on the type and size of the bioreactor 110, and may include gas compressors, paddles or impellers for agitation, valves, control electronics, equipment used to process biomass, dryers, and the like.

The electricity required to operate the bioreactor 110 may be supplied from the electricity grid 112 or from a local power generator 118. The origin of the electricity provided from the electricity grid is not considered particularly limited and may include renewable, alternative, or conventional sources of power. The ratio of the electricity sourced from the electricity grid 112 or from a local power generator 118 may be controlled by any suitable method. In some embodiments, the local power generator 118 generates 100%, at least 90%, or at least 60% of the electricity required to operate the bioreactor 110. In other embodiments, the electricity grid 112 provides 100%, at least 90%, or at least 60% of the electricity required to operate the bioreactor. In still other embodiments, local power generator 118 may generate electricity in excess of the requirements for the bioreactor 110.

By using excess produced natural gas to generate electricity by the local power generator 118, the costs associated with operating the bioreactor 110 may be reduced to economically feasible levels. In some embodiments, dynamic control system 104 may monitor and control the contribution from the electricity grid 112 or the local power generator 118 to the bioreactor 110. Dynamic control system 104 may also convert system 100 to generate power beyond the requirements of system 100. For example, in cases where electricity prices are higher on the market in comparison to protein generation, the dynamic control system 105 may focus the system 100 to power generation from local power generator 118 for sale to a local municipality. In some embodiments, excess electricity 125 generated may be routed through dynamic control system 104 and to electricity grid 112, however, in other embodiments, electricity may route to the electricity grid 112. Moreover, in either case, electricity may route to the electricity grid directly or through one or more intermediates or distributors.

The balance of electricity provision may be shifted among the electricity grid 112 or the local power generator 118 depending on a number of factors such as cost balancing between the sources, availability, power demand for various system components, economic factors such as market value of SCP, market value of generated electricity, and the like. In one example, a bioreactor 110 may be powered primarily by a local power generator 118 during "peak times" in which the costs of power from the electricity grid 112 may increase, or where availability decreases, as in the case of solar or wind power. Conversely, power from the electricity grid 112 may be preferred where electrical grid supply exceeds demand, and the price is correspondingly lower. The use of a local power generator 118 consuming stranded natural gas may also increase the reliability of the electricity supply in remote locations, where the electricity grid 112 may be underpowered or spotty.

Following propagation in bioreactor 110, the hydrocarbon degrading microbes may be collected as a biomass 122. The biomass 122 may be processed to generate a protein source by any suitable process, which may include separation, processing, and treatments steps. Biomass processing may include sterilization, centrifugation, nucleic acid reduction, drying, and the like. Harvested SCP may then be used as a protein source for other microorganisms; shellfish or other invertebrates; livestock such as pigs and chickens; pets; fish; birds; and mammals, but may be subject to various regulations and/or recommendations from agencies and governmental bodies such as the Food and Agriculture Organization (FAO).

Methods disclosed herein may also include one or more subsystems for recycling heat and energy back to useful processes within system 100. In some embodiments, excess heat 124 generated from power generator 118 during the provision of power to bioreactor 110 may be used to cool bioreactor 110. In some embodiments, an absorption refrigerator 126 may convert excess heat 124 to a source of cooling 128 for bioreactor 110. The energy from excess heat 124 may be sufficient to power absorption refrigerator 126 in some cases, or direct combustion of natural gas, hydrocarbon exploration, or similar processes may be used to provide an additional heat source.

Other uses for excess heat 124 may include the production of steam and/or hot water for various system 100 processes and/or other processes, including use in hydrocarbon exploration or production, such as extracting petroleum-like products from oil sands, gasification of coal, pyrolysis of oil shale, and the like.

Figure 2B:
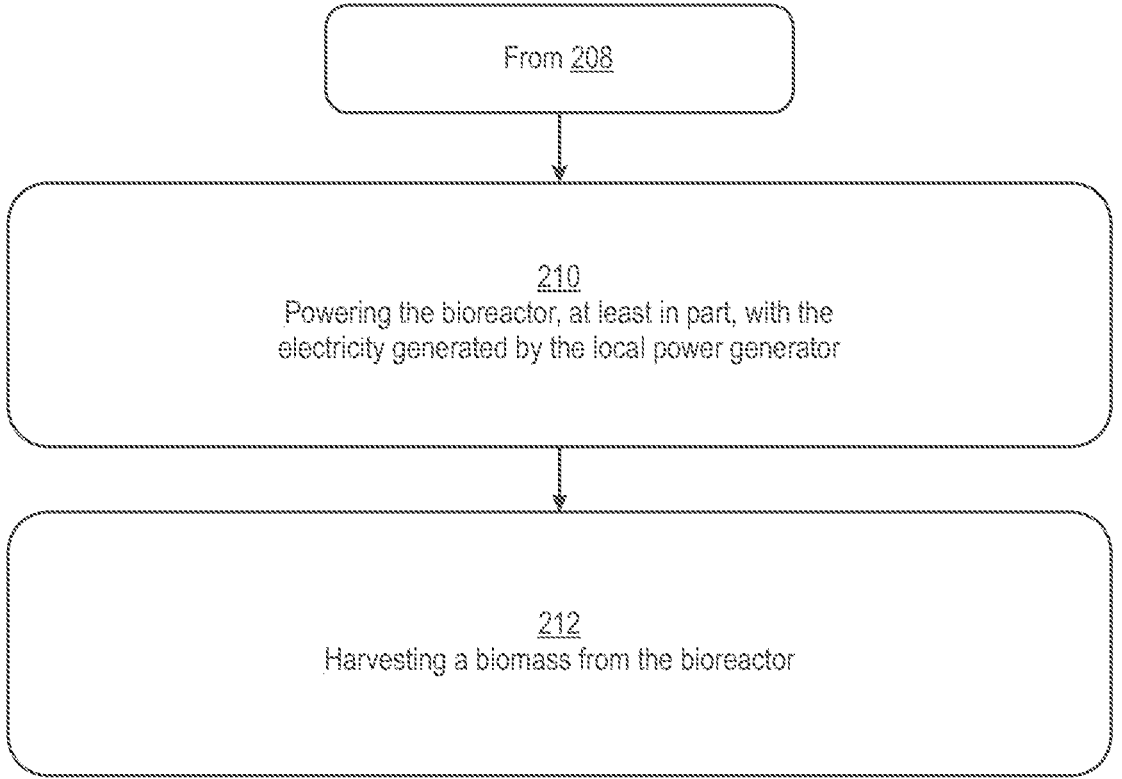

A flow diagram describing the steps of the overall method 200 of converting natural gas to SCP is shown in FIGS. 2A and 2B. At 202 in FIG. 2A, a natural gas stream obtained from a hydrocarbon production site or storage vessel. A first fraction of the natural gas stream is then directed to a bioreactor containing a propagating hydrocarbon degrading microbes at 204, while a second fraction of the natural gas stream is directed to a local power generator and converting the natural gas to electrical power and heat at 206. At 208, a dynamic control system may be used to balance the first natural gas stream to the bioreactor and the second natural gas stream to the local power generator.

Balancing natural gas inputs to the bioreactor and the local power generator may include using a dynamic control system to calculate the amount of electrical power to distribute from the power generator to supply the bioreactor. In some cases, the dynamic control system may also monitor and control the balance of electricity between an electricity grid and the local power generator. The balance of natural gas and/or electricity may be modified based on a number of factors or user inputs, including the power demand from the reactor, the economic value of produced SCP, and the availability and/or price of electricity from the electricity grid (due to peak load times or other similar factors). In some embodiments, it may be more economic to focus the system to electricity generation, depending on a value comparison of electricity generation and SCP production. In times where the price of electricity is higher than the price of SCP, for example, bioreactor operations and SCP production may be reduced and the natural gas directed primarily to the local power generator. Bioreactor production may be reduced by any method known in the art, such as reducing temperature, nutrient feed, agitation, natural gas input, and the like.

Returning to FIG. 2B, at 210, the bioreactor is powered, at least in part, with the electricity generated by the local power generator. Following propagation, the hydrocarbon degrading microbes within the bioreactor is harvested as a biomass at 212. In some embodiments, the biomass may be processed to a protein source by any suitable methods known in the art.

Various aspects of the systems and methods described herein, such as operation of the dynamic control system may utilize computer systems, such as to process data received from the system (e.g., sensors, equipment associated with hydrocarbon production, equipment associated with natural gas separation from the produced hydrocarbons, operation of the bioreactor, and the like) to determine operational parameters (e.g., natural gas pressure, natural gas flow rate, retrieval of economic data regarding electricity and SCP, and the like) of the methods and systems described herein. Such systems and methods may include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can be performed using computing devices or processor-based devices that include a processor; a memory coupled to the processor; and instructions provided to the memory, wherein the instructions are executable by the processor to perform the methods described herein. The instructions can be a portion of code on a non-transitory computer readable medium. Any suitable processor-based device may be utilized for implementing all or a portion of embodiments of the present techniques, including without limitation personal computers, networks of personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

Computing devices or processor-based devices may be configured to perform through wired and/or wireless communication with remote devices, e.g., other computer systems, over a network, and can be, for non-limiting example, remote desktop connection interfaces, ethernet adapters, other local area network (LAN) adapters, WIFI, LTE, SCADA. Communications protocols for managing communication are known, and may include IEEE 802.11, IEEE 802.3, USB-compatible, Bluetooth, and the like. Embodiments disclosed herein include:

Embodiments disclosed herein include:

A. Methods comprise: providing a natural gas stream; directing a first fraction of the natural gas stream to a bioreactor comprising hydrocarbon degrading microbes; directing a second fraction of the stream to a local power generator and converting the natural gas stream to electricity and heat; powering, at least in part, the bioreactor with the electricity generated by the local power generator; and harvesting the hydrocarbon degrading microbes from the bioreactor as a biomass.

B. Methods comprise: providing a natural gas stream; directing a first fraction of the natural gas stream to a bioreactor comprising a propagating culture of hydrocarbon degrading microbes; directing a second fraction of the gas stream to a local power generator and converting the natural gas stream to electricity and heat; using a dynamic control system to balance of the gas stream to the first fraction and the second fraction based on one or more of the availability of electricity from an electricity grid and the price of electricity from the electricity grid; powering, at least in part, the bioreactor with the electricity generated by the local power generator; and harvesting the hydrocarbon degrading microbes from the bioreactor as a biomass.

C. A system comprising: a natural gas stream; a bioreactor propagating hydrocarbon degrading microbes and receiving at least a portion of the natural gas stream; a local power generator receiving at least a portion of the natural gas stream, the power generator connected to the bioreactor and providing at least a portion of electrical power thereto; an electricity grid connected to the bioreactor and capable of providing at least a portion of electrical power thereto; and a dynamic control system connected to the bioreactor, the local power generator, and the electricity grid, the dynamic control system controlling amount of electrical power output from the power generator and the electricity grid to the bioreactor based on one or more user inputs.

Embodiments A, B, and C may have one or more of the following additional elements in any combination.

Element 1: wherein the bioreactor is powered, at least in part, by an electricity grid, and further comprising a dynamic control system that balances the power demands of the bioreactor between the electricity grid and the local power generator based on one or more of the availability of electricity from the electricity grid and the price of electricity from the electricity grid.

Element 2: further comprising using a heat output from the local power generator as an input for an absorptive cooler that provides cooling to the bioreactor.

Element 3: wherein the power generator generates at least 60% of the power required to operate the bioreactor.

Element 4: wherein the power generator generates at 100% of the power required to operate the bioreactor.

Element 5: further comprising processing the biomass to produce a protein feedstock.

Element 6: wherein the hydrocarbon degrading microbes comprise a methanotrophic bacteria.

Element 7: wherein the hydrocarbon degrading microbes comprise an archae or fungi.

Element 8: wherein the gas stream is sourced from hydrocarbon production.

Element 9: wherein the dynamic control system further balances the power demands of the bioreactor between the electricity grid and the local power generator.

Element 10: wherein the electricity converted by the local power generator produced is in excess of the demands of the bioreactor, the method further comprising selling the excess electricity to the electricity grid.

Element 11: further comprising reducing the bioreactor production and maximizing production of excess electricity Element 12: wherein the user inputs comprise one or more of the availability of electricity from an electricity grid and the price of electricity from the electricity grid.

By way of non-limiting example, exemplary combinations applicable to A and B include, but are not limited to, 1 and any one or more of 2 to 11; 2 and any one or more of 1 and 3 to 11; 3 and any one or more of 1 to 2 and 4 to 11; 4 and any one or more of 1 to 3 and 5 to 11; 5 and any one or more of 1 to 4 and 6 to 11; 6 and any one or more of 1 to 5 and 7 to 11; 7 and any one or more of 1 to 6 and 8 to 11; 8 and any one or more of 1 to 7 and 9 to 11; 9 and any one or more of 1 to 8 and 10 to 11; 10 and any one or more of 1 to 9 and 11; 11 and any one or more of 1 to 10. By way of non-limiting example, exemplary combinations applicable to C include, but are not limited to, 12.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

What is claimed is:

1. A method comprising:
   providing a natural gas stream;
   directing a first fraction of the natural gas stream to a bioreactor comprising hydrocarbon degrading microbes;
   directing a second fraction of the stream to a local power generator and converting the natural gas stream to electricity and heat;
   powering, at least in part, the bioreactor with the electricity generated by the local power generator; and
   harvesting the hydrocarbon degrading microbes from the bioreactor as a biomass.

2. The method of claim 1, wherein the bioreactor is powered, at least in part, by an electricity grid, and further comprising a dynamic control system that balances the power demands of the bioreactor between the electricity grid and the local power generator based on one or more of the availability of electricity from the electricity grid and the price of electricity from the electricity grid.

3. The method of claim 1, further comprising using a heat output from the local power generator as an input for an absorptive cooler that provides cooling to the bioreactor.

4. The method of claim 1, wherein the power generator generates at least 60% of the power required to operate the bioreactor.

5. The method of claim 1, wherein the power generator generates at 100% of the power required to operate the bioreactor.

6. The method of claim 1, further comprising processing the biomass to produce a protein feedstock.

7. The method of claim 1, wherein the hydrocarbon degrading microbes comprise a methanotrophic bacteria.

8. The method of claim 1, wherein the hydrocarbon degrading microbes comprise an archae or fungi.

9. The method of claim 1, wherein the natural gas stream is sourced from hydrocarbon production.

10. A method comprising:
    providing a natural gas stream;
    directing a first fraction of the natural gas stream to a bioreactor comprising a propagating culture of hydrocarbon degrading microbes;
    directing a second fraction of the gas stream to a local power generator and converting the natural gas stream to electricity and heat;
    using a dynamic control system to balance the first fraction and the second fraction based on one or more of the availability of electricity from an electricity grid and the price of electricity from the electricity grid;
    powering, at least in part, the bioreactor with the electricity generated by the local power generator; and
    harvesting the hydrocarbon degrading microbes from the bioreactor as a biomass.

11. The method of claim 10, wherein the dynamic control system further balances the power demands of the bioreactor between the electricity grid and the local power generator.

12. The method of claim 10, further comprising using a heat output from the local power generator as an input for an absorptive cooler that provides cooling to the bioreactor.

13. The method of claim 10, further comprising processing the biomass to produce a protein feedstock.

14. The method of claim 10, wherein the power generator generates at least 60% of the power required to operate the bioreactor.

15. The method of claim 10, wherein the power generator generates 100% of the power required to operate the bioreactor.

16. The method of claim 10, wherein the hydrocarbon degrading microbes comprise a methanotrophic bacteria.

17. The method of claim 10, wherein the electricity converted by the local power generator produced is in excess of the demands of the bioreactor, the method further comprising selling the excess electricity to the electricity grid.

18. The method claim 17, further comprising reducing the bioreactor production and maximizing production of excess electricity.

* * * * *